United States Patent [19]

Khaw et al.

[11] Patent Number: 4,859,450

[45] Date of Patent: Aug. 22, 1989

[54] METHOD OF NMR IMAGING USING ANTIBODY TO CARDIAC MYOSIN

[75] Inventors: Ban-An Khaw, Milton, Herman K. Gold, Boston, Mark Goldman, Weston, all of Mass.

[73] Assignee: The General Hospital Corporation, Boston, Mass.

[21] Appl. No.: 938,988

[22] Filed: Dec. 8, 1986

Related U.S. Application Data

[63] Continuation of Ser. No. 640,305, Aug. 13, 1984, abandoned.

[51] Int. Cl.$^4$ .......................... A61K 49/00; A61B 5/05; A61B 6/00
[52] U.S. Cl. ............................................ 424/9; 424/4; 424/85.8; 128/653; 128/654
[58] Field of Search .................. 424/4, 9, 85; 436/173, 436/806, 548; 128/653, 654

[56] References Cited

U.S. PATENT DOCUMENTS

| | | | |
|---|---|---|---|
| 4,352,751 | 10/1982 | Wieder et al. | 435/7 |
| 4,454,106 | 6/1984 | Ganson et al. | 424/9 |
| 4,647,447 | 3/1987 | Gries et al. | 424/4 |

FOREIGN PATENT DOCUMENTS

| | | | |
|---|---|---|---|
| 8633082 | 1/1983 | Australia | 424/9 |
| 0071564 | 2/1983 | European Pat. Off. | 424/9 |

OTHER PUBLICATIONS

Lauterbur et al., Frontiers of Biological Energetics, vol. 1 (1978), pp. 752–759.

Unger et al., "Magnetic Resonance Imaging Using Gadolinium Labeled Monoclonal Antibody", *Investigative Radiology*, vol. 20, Oct. 1985, pp. 693–700.

*Primary Examiner*—Robert J. Warden
*Assistant Examiner*—Stephen C. Wieder

[57] ABSTRACT

An in vivo NMR imaging method comprising administering to a human patient an NMR contrast agent comprising a specific affinity organic substituent complexed with a paramagnetic substance and subjecting the patient to NMR imaging.

7 Claims, No Drawings

METHOD OF NMR IMAGING USING ANTIBODY TO CARDIAC MYOSIN

This is a continuation of co-pending application Ser. No. 640,305 filed on Aug. 13, 1984, abandoned.

BACKGROUND OF THE INVENTION

This invention relates to diagnostic NMR imaging.

NMR imaging has been used in medical diagnosis for a number of years. It is known that certain paramagnetic substances, e.g., ionic manganese, can reduce the spin lattice relaxation time (T1) of surrounding water protons in vitro, and manganese has been used in in vivo experiments to provide NMR contrast between healthy and infarcted myocardial tissue.

Lauterbur (1978) Frontiers of Biological Energetics 1, 752 describes the use of ionic manganese to provide such contrast in dogs in which myocardial infarctions were induced prior to manganese administration and NMR imaging: "The ischemic region of the heart is clearly delineated by the relaxation rates and by the manganese concentrations."

Brady et al. (1982) Radiology 144, 343 discussed Lauterbur, supra: "using in vitro NMR spectroscopic analysis of tissue, Lauterbur et al. demonstrated that the manganese distribution to normal myocardium allowed differentiation between normal and ischemic or infarcted tissue, due to enhanced proton relaxation time." Brady et al. go on to report similar experimental results: "(T)hose (hearts) with manganese demonstrated a clearly demarcated zone of reduced signal intensity consistent with the ischemic zone."

SUMMARY OF THE INVENTION

In general, the invention features an in vivo NMR imaging method which includes administering to a human patient an NMR contrast agent composed of a specific affinity organic substituent complexed with a paramagnetic substance and subjecting the patient to NMR imaging.

More particularly, the invention features a method of enhancing the contrast between NMR spectra of different first and second tissues in a human patient, the first tissue being in contact with aqueous liquid, the method including administering to the human patient an NMR contrast agent composed of a specific affinity organic substituent having greater affinity for the first ("target") tissue than for the second tissue, the specific affinity substituent being complexed with a paramagnetic substance capable of reducing the spin lattice relaxation time of protons in the water of the aqueous liquid. (As used herein, "tissue" means any biological entity in a patient distinguishable from other entities, e.g., organs, regions of organs, cell types, tumors, clots, etc.)

In a preferred embodiment of the invention, the first tissue is infarct - damaged cardiac tissue, the second tissue is comparatively less damaged cardiac tissue, and the specific affinity substituent is an antibody specific for cardiac myosin.

In other preferred embodiments, the paramagnetic substance is further characterized in that one gram formula weight has a magnetic susceptibility less than that of iron and greater than $500 \times 10^{-4}$ cgs. Preferably the paramagnetic substance, when complexed with the specific affinity substituent, retains a magnetic susceptibility of at least $300 \times 10^{-4}$ cgs.

In other preferred embodiments, the paramagnetic substance is an element (e.g., gadolinium or manganese) which has at least two unpaired electrons and, when complexed with the specific affinity substituent, has at least one unpaired electron sufficiently exposed to decrease spin lattice relaxation time of water protons.

The invention provides for delivery of NMR contrast agents to targeted tissues, e.g., damaged cardiac muscle or tumor loci, in a highly specific, targeted manner. This targeting permits the use of small amounts of contrast agent, and minimizes background noise. The invention expands the capabilities of NMR as a diagnostic tool, permitting its use to obtain information formerly available, if at all, only by methods which were either invasive (e.g., biopsy) or which involved exposure to potentially harmful substances (e.g., targeted radioisotopes). For example, the NMR contrast and specificity provided by the invention permits detailed cardiac diagnostic information to be obtained by NMR imaging. Following myocardial infarction, accurate assessment of infarct size and location is important both for evaluating proposed medical interventions designed to limit myocardial necrosis; and for reaching clinical decisions in overall patient care. The invention provides such information with greater precision than even isotopic techniques such as single photon emission tomography using radiopharmaceuticals. The invention can similarly provide crucial diagnostic information on primary and secondary tumor loci.

Other features and advantages of the invention will be apparent from the following description of the preferred embodiments thereof, and from the claims.

DESCRIPTION OF PREFERRED EMBODIMENTS

We now describe preferred embodiments of the invention.

Composition of Specific-Affinity Contrast Agents

The contrast agents of the invention are, as stated above, composed of a specific affinity organic substituent complexed with a paramagnetic substance. The specific affinity substituent exhibits a selective affinity for the target tissue to which the paramagnetic substance is to be delivered.

The specific affinity substituent of the contrast agent can be, e.g., an antigen or an antibody specific for the antigen. If the contrast agent contains the antibody, the antigen is relatively more plentiful or more accessible in the target tissue, compared to other tissues. If the contrast agent contains the antigen, the target tissue contains more or more accessible antibody to the antigen. One example of a useful antibody, discussed in more detail below, is anti-cardiac myosin antibody, which provides the specific affinity portion of a contrast agent which enhances contrast between normal cardiac tissue and infarcted cardiac tissue, in which cardiac myosin is more accessible. Other antibodies useful in contrast agents are antibodies against tumor antigens; antibodies against hormones, e.g., human chorionic gonadotropin (hCG), which are diagnostic for certain types of tumors; antibodies against biological particles, e.g., white blood cells, red blood cells, and platelets; anticarcinoembryonic antigen (CEA), which specifically binds to certain tumors; and anti-alpha feto protein, which specifically binds to liver tissue. The antibody can be polyclonal or, more preferably, monoclonal and, if IgG, can be the entire antibody or just the Fab portion. The entire antibody will have the advantage of being excreted more slowly than the Fab portion, but will, because of its comparatively larger size, be taken up by tissue more slowly, rendering the imaging procedure more time-consuming.

The contrast agents can contain not only antigens or antibodies, but other macromolecules as well, in particular other proteins, which exhibit a preferential affinity for a target tissue; an example is fibrinogen, which specifically binds to clots.

The paramagnetic portion of the contrast agents of the invention preferably is a paramagnetic element or compound which has one or more unpaired electrons which produce an isotropic magnetic field in response to an applied magnetic field, has a magnetic susceptibility less than that of iron and greater than about $500 \times 10^{-4}$ cgs (and $300 \times 10^{-4}$ cgs when complexed with the specific affinity portion of the contrast agent), exhibits a pharmaceutically acceptable toxicity level when complexed with the specific affinity portion of the contrast agent, and does not impair the ability of the specific affinity portion to so bind.

Because it is the unpaired electrons which provide contrast enhancement, it is desirable that the paramagnetic substance have as many such unpaired electrons as possible, most preferably four or more. An additional factor to be taken into account when selecting a paramagnetic substance is size; larger molecules generally advantageously provide greater exposure of their unpaired electrons to the surrounding water. Preferred paramagnetic elements are manganese, which has five unpaired electrons, and gadolinium, which has seven. Another suitable paramagnetic element is rubidium. These elements are capable of producing isotropic magnetic fields which give rise to a reduction in T1 (as opposed to elements which primarily produce anisotropic fields, giving rise to chemical shifts, rather than reductions in T1).

Preparation of Contrast Agents

The paramagnetic and specific affinity portions of the contrast agents are complexed so as to minimize the toxicity of the paramagnetic portion, preserve the specificity of the specific affinity portion, preserve the paramagnetic quality of the paramagnetic portion, and maximize exposure of the unpaired electrons of the paramagnetic portion to surrounding aqueous liquid. Preferred complexing agents are bifunctional chelating agents, e.g., diethylenetriaminepentaacetic acid (DTPA) and ethylenediaminetetraacetic acid (EDTA).

Generally, the first step in preparing contrast agents in which the specific affinity and paramagnetic portions are coupled via a bifunctional chelating agent is to react the chelating agent and the specific affinity molecule to covalently bond the two; where the specific affinity molecule is a protein, a peptide bond is generally formed. This reaction is carried out under conditions which prevent denaturation of the protein, i.e., at about neutral pH and at room temperature; generally, suitable pH and temperature ranges are, respectively, about 6-8 and about 4° C.-37° C.

The next step is to react the chelating agent, bonded to the specific affinity molecule, with the paramagnetic substance. This reaction is also carried out under conditions which prevent denaturation of the protein.

The resulting contrast agent is stored in lyophilized form or in physiological buffer until use. Alternatively, the chelating agent bonded to the specific affinity substance can be stored separately from the paramagnetic substance, and the two mixed to form the contrast agent just prior to use.

Another approach involves the use of a polyfunctional carrier, e.g., poly-lysine, to which many chelating agent molecules can be covalently attached. DTPA molecules, for example, can be attached to poly-lysine sites by the carboxycarbonic anhydride reaction; the specific affinity portion of the contrast agent can then be attached to some of the DTPA molecules as described above. The poly-lysine "tree" will enrich the DTPA molar concentration (and hence the manganese concentration) per mole of antibody, thereby enhancing NMR contrast while minimizing the amount of antibody required. The concept of using such a polyfunctional carrier is the sole conception of one of the undersigned, Ban-An Khaw.

Use

The NMR contrast agents can be used as diagnostic agents for a variety of medical disorders; the organic substituents are chosen so that the paramagnetic substance is delivered to the target tissue to enhance the contrast between the NMR spectra of that tissue and other tissues; contrast is enhanced because the unpaired electrons of the paramagnetic substance cause a decrease in the spin lattice relaxation time of the protons in the water molecules in contact with the target tissue.

The contrast agent is preferably administered intravenously in physiological buffer. Dosage will vary, depending in part on the composition of the contrast agent. For example, a contrast agent employing a high affinity antibody complexed with a strong paramagnetic substance will require a lower dosage than lower affinity, weaker contrast agents. In general, intravenous dosage will be in the range of about 0.2-500 mg/kg, preferably about 1-2 mg/kg.

Arterial administration, which is less preferred, requires on the order of one tenth the dosage of intravenous administration.

Following administration of the contrast agent, conventional NMR imaging is carried out; the details of the procedure will be governed by the diagnostic information sought. Use of the contrast agents can provide information regarding size, location, and characterization of primary and secondary tumor loci or of tissue damage sites, e.g., myocardial infarcts.

Cardiac Contrast Agent

An NMR contrast agent for enhancing the contrast between infarct-damaged cardiac muscle and normal or less damaged cardiac muscle was prepared by complexing anti-cardiac myosin monoclonal antibody with manganese using DTPA, as follows.

Anti-cardiac myosin IgG monoclonal antibody was produced and purified using conventional techniques, as generally described in Khaw et al. (1984) Hybridoma 3, 11. Fab fragments were prepared conventionally by digestion with mercuri-papain.

Anti-myosin Fab was covalently bonded to DTPA by the carboxycarbonic anhydride method described in Krejcarek et al. (1977) Biochem. Biophys. Res. Comm. 77, 581; and Khaw et al. (1982) J. Nucl. Med. 23(11), 1011. The resulting compound, in 0.15 M NaCl, was then added to excess manganese chloride (100 mg) and the mixture stirred for fifteen minutes at room temperature.

Excess manganese chloride was removed by desalting the reaction product on a Sephadex G-25 column (10 ml), and then dialyzing it against saline for 1-2 hours. Analysis of purified contrast agent using $^{14}$C-labeled DTPA indicated that the maximum DTPA: antimyosin molar ratio was 3-4:1.

The contrast agent was then used to provide data on induced myocardial infarctions in dogs, as follows.

Thirteen adult mongrel dogs (of average weight of about 20 kg) were anesthetized, intubated, and placed on a respirator. Each dog's chest was opened in the fifth intercostal space and a 1 cm segment of the left anterior descending coronary artery was isolated, distal to the first septal perforator and its first diagonal branch. A 0.7 mm catheter was inserted into a side branch of the isolated arterial segment, a reversible snare occlusion was placed proximal to the catheter, and the artery was occluded for a three hour period to induce myocardial infarction. Electrocardiogram data were recorded continuously for the three hour period, after which time the snare was released.

After 15 min of reflow, nine of the dogs received injections, into the left arterior descending coronary artery, of 2-4 mg of the above-described contrast agent in physiological buffer; assuming four molecules of manganese per molecule of DTPA, the manganese dose each dog received was about 30-40 $\mu$g. As a control, four dogs received 2-4 mg of manganese chloride.

Hearts from treated dogs were excised and subjected to NMR imaging using a small (8 cm) bore superconducting magnet with a field strength of 1.44 Tesla ($^1$H resonance frequency of 61.4 MHz). Images were obtained as tomograms transverse to the long axis of the heart from apex to base using a spin echo pulse sequence (TR 200, TE 30 ms) heavily weighted to obtaining T1 information. Plane selection was by selective excitation and in-plane spatial coding by 2D Fourier transformation.

Following NMR imaging, hearts were sliced transversely at approximately the same planes as the NMR images and photographed for comparison with NMR data. In addition, pathologic evaluation was performed on the hearts of seven of the dogs to localize myocardial infarctions and to provide a basis of comparison with the NMR data.

In eight of the nine dogs into which the contrast agent had been injected, SE 200/30 images demonstrated a marked increase in signal intensity consistent with a short T1 in the region of the heart supplied by the left anterior descending coronary artery. In the seven animals on which pathological examination was carried out, corresponding slices confirmed myocardial necrosis in the same region exhibiting abnormal NMR signal intensities. The one dog which had received the contrast agent and which did not exhibit abnormal NMR signal intensity proved on histologic examination to have no myocardial necrosis.

The four control dogs exhibited no changes in signal intensity between normal and infarcted regions.

It is believed that the contrast agent works as follows. Interruption of the blood supply to a region of the heart causes necrosis with accompanying sarcolemal disruption, exposing cardiac myofilaments. The anti-cardiac myosin of the contrast agent, whose biological activity had not been adversely affected by its chemical association with manganese, specifically binds to the exposed myosin, but not to healthy tissue where the myosin of intact cells has not been exposed; necrotic myocardial tissue is thus labelled with manganese.

The manganese, although partially shielded by the DTPA, sufficiently exposes its unpaired electrons to reduce T1 of the protons of the water in the aqueous liquid in contact with the necrotic myocardial tissue, providing NMR signal contrast between necrotic and healthy tissue. It is believed that T1 reduction is further enhanced by the size of the contrast agent, which is much greater than that of ionic manganese alone. This greater size advantageously reduces the rate at which the manganese tumbles in the vicinity of the surrounding water; this reduced tumbling rate contributes to T1 reduction.

The contrast agent also exhibits very low toxicity, compared to that of ionic manganese.

Other embodiments are within the following claims.

We claim:

1. A method of enhancing the contrast between NMR spectra of infarct-damaged cardiac tissue and comparatively less damaged cardiac tissue in a human patient, said method comprising administering to said human patient an NMR contrast agent comprising an antibody to cardiac myosin complexed with a paramagnetic substance capable of reducing the spin lattice relaxation time of protons in the water of aqueous liquid in contact with said infarct-damaged cardiac tissue, and imaging said human patient.

2. The method of claim 1 wherein said paramagnetic substance is an element having at least two unpaired electrons.

3. The method of claim 2 wherein said paramagnetic substance is manganese.

4. The method of claim 2 wherein said paramagnetic substance is gadolinium.

5. The method of claim 1 wherein said paramagnetic substance is further characterized in that one gram formula weight of said substance has a magnetic susceptibility less than that of iron and greater than $500 \times 10^{-4}$ cgs.

6. The method of claim 5 wherein said paramagnetic substance, when chemically attached to said organic substituent via a chelating agent, has a magnetic susceptibility of at least $300 \times 10^{-4}$ cgs.

7. The method of claim 1 wherein said paramagnetic substance, when chemically attached to said organic substituent via a chelating agent, has at least one unpaired electron which is sufficiently exposed to said aqueous liquid to decrease said spin lattice relaxation time.

* * * * *